United States Patent [19]

Berneth et al.

[11] Patent Number: 6,046,290
[45] Date of Patent: Apr. 4, 2000

[54] PHOTOADDRESSABLE SIDE GROUP POLYMERS OF HIGH SENSITIVITY

[75] Inventors: Horst Berneth; Uwe Claussen, both of Leverkusen; Serguei Kostromine, Swisttal; Ralf Neigl, Leverkusen; Joachim Rübner; Ralf Ruhmann, both of Berlin, all of Germany

[73] Assignee: Bayer Aktiengesellschaft, Leverkusen, Germany

[21] Appl. No.: 08/905,659

[22] Filed: Aug. 4, 1997

[30] Foreign Application Priority Data

Aug. 7, 1996 [DE] Germany ............ 196 31 864

[51] Int. Cl.[7] .............. C08F 220/36; C08F 220/34; C08F 220/42

[52] U.S. Cl. .............. 526/263; 526/258; 526/299; 526/300; 526/312; 526/320; 526/326

[58] Field of Search ............ 526/299, 300, 526/312, 263, 258, 320, 326

[56] References Cited

U.S. PATENT DOCUMENTS

| | | | |
|---|---|---|---|
| 4,631,328 | 12/1986 | Ringsdorf et al. | 526/259 |
| 5,098,978 | 3/1992 | Riepl et al. | 528/15 |
| 5,641,846 | 6/1997 | Bieringer | 526/292.2 |

FOREIGN PATENT DOCUMENTS

| | | |
|---|---|---|
| 0 090 282 | 3/1982 | European Pat. Off. . |
| 276 297 B5 | 10/1988 | Germany . |
| 887574 | 7/1981 | U.S.S.R. . |

OTHER PUBLICATIONS

Kostromin, et al., "Thermotropic liquid–crystalline polymers XXVI. Synthesis of comb–like polymers with oxygen containing spacers and a study of their phase transitions," Liquid Crystals, 1987, vol. 2, No. 2, 195–200.

Akelah, Preparation and Application of Functional Polymers–II, Eur. Polym. J. vol. 18, pp. 559 to 561, 1982.

Ringsdorf et al., "Electro–optical effects of azo dye containing liquid crystalline copolymers," Makromol. Chem. 185, 1327–1984.

B. Vollmer, Grundriss der Makromolekularen Chemie [Principles of Macromolecular Chemistry], pp. 406–410, Springer–Verlag, Heidelberg 1962.

Primary Examiner—Fred Zitomer
Attorney, Agent, or Firm—Foley & Lardner

[57] ABSTRACT

The invention provides an optical method which permits, with the aid of 6 simple measurements, a conclusion regarding the suitability of antennas (groups which can absorb electromagnetic radiation) for incorporation into photoaddressable polymers.

2 Claims, No Drawings

PHOTOADDRESSABLE SIDE GROUP POLYMERS OF HIGH SENSITIVITY

The invention relates to photoaddressable side group polymers in which a high birefringence can be induced by irradiation, so that they are suitable for the production of components for storage of optically available information or as optically switchable components.

Photoaddressable side group polymers which have been recommended are special branched polymers: side groups of different types, of which one type (called "A") can absorb electromagnetic radiation and another type (called "M") is a mesogenic group anisotropic in shape, are positioned on a linear backbone, connected via molecular parts which act as spacers.

So that the interaction of the mesogenic groups is not impeded, in the past the mesogenic groups have usually been coupled to the spacing group via an oxygen atom, because it has been assumed to date that higher-valency atoms with their substituents in this position impede the interaction and therefore the photoaddressability because of their steric requirement.

The mechanism of photoaddressed orientation is probably based on the possibility of achieving an orientation of the mesogenic groups and therefore a change in the state of order by electromagnetic radiation. However, the photoaddressable polymers known to date still have the disadvantage that the changes in the state of order which can be produced are too small, the change in the state of order takes place too slowly and/or the patterns written in slowly fade again during storage.

The object of the invention was therefore to provide polymers which do not have these disadvantages or have them to a lesser extent.

Surprisingly, a connection has now been found between the experimentally determinable interaction of the group A, which can absorb electromagnetic radiation, with respect to a standard and the quality of the photoaddressability of the polymer. This finding allows the suitability of the groups A to be tested before their incorporation into the polymer.

The invention thus relates to polymers which have a main chain which acts as a backbone and, branching therefrom, covalently bonded side groups of the formulae

 (I) and

 (II)

wherein
$S^1$ and $S^2$ denote the atoms O or S or the radical $NR^0$,
$R^0$ denotes hydrogen or $C_1$-$C_4$-alkyl,
$T^1$ and $T^2$ denote the radical $(CH_2)_n$, which can optionally be interrupted by —O—, —$NR^0$— or —$OSiR^0{}_2O$— and/or can optionally be substituted by methyl or ethyl,
$Q^1$ and $Q^2$ denote a direct bond, —O—, —COO—, —OCO—, —$CONR^0$—, —$NR^0CO$— or —$NR^0$—, or
$S^1T^1Q^1$ or $S^2T^2Q^2$ denotes a bivalent group of the formula

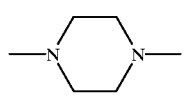

A denotes a unit which can absorb electromagnetic radiation,
M denotes a mesogenic unit anisotropic in shape and n denotes an integer from 2 to 12,
characterized in that A has an extinction modulus $\Delta\Delta E$ of greater than 0.2 (measured as described below).

For the purposes of the invention, the value $\Delta\Delta E$ is measured on a compound of the formula H—$Q^1$—A or $HS^1T^1Q^1A$ wherein $Q^1$, $S^1$, $T^1$ and A have the abovementioned meaning and H represents the hydrogen radical.

The extinction modulus $\Delta\Delta E$ is determined from the changes in extinction $\Delta E$ of the longwave flank of the absorption band of 3 solutions of the following substances, that is to say Solution A H—$Q^1$—A or $HS^1T^1Q^1A$ is dissolved in the lowest possible concentration in a solvent which has the lowest possible polarity. The concentration is preferably chosen here such that the steepest possible edge results when the absorption is measured. In the case of dyestuffs, which as a rule have a high molar extinction, this concentration is preferably $10^{-3}$ molar.

Solution B The standard is dissolved in the same solvent in the highest possible concentration, preferably 1 molar, and the absorption edge is recorded.

Solution C This solution comprises H—$Q^1$—A or $HS^1T^1Q^1A$ and the standard in the concentrations of solutions A and B.

3 absorption edges are thus obtained: that of the standard, which in general is at a short wavelength, and the absorption edge of solution A and the edge of solution C, which is shifted parallel to this to a long wavelength.

On the longest-wavelength edge, that is to say of solution C, the wavelength belonging to the extinction 0.8 defines the reference wavelength $\lambda$. The extinction values E of the three solutions A, B and C are now in each case read off at the wavelengths $\lambda$ and $\lambda+50$, where $$E_{solution\ C} > E_{solution\ A} > E_{solution\ B}.$$

To determine the value of $\Delta E$, the following differences are obtained for the wavelengths $\lambda$ and $\lambda+50$:

$$\Delta E_A = E\ (\lambda)_{solution\ A} - E\ (\lambda+50)_{solution\ A}$$

$$\Delta E_B = E\ (\lambda)_{solution\ B} - E\ (\lambda+50)_{solution\ B}$$

$$\Delta E_C = E\ (\lambda)_{solution\ C} - E\ (\lambda+50)_{solution\ C}$$

From these three differences, the increase in extinction of the dyestuff due to the presence of the standard is obtained as the difference $\Delta\Delta E$:

$$\Delta\Delta E = \Delta E_C - (\Delta E_B + \Delta E_A)$$

The standard should be as polar and/or polarizable as possible. The polarity of the solvent should be as low as possible.

In a preferred form, 1,3-dinitrobenzene is used as the standard and dioxane is used as the solvent.

As explained above, A should be able to absorb electromagnetic radiation. The absorption maxima ($\lambda_{max}$) of preferred groups A can be in the near IR, in the range of visible light or in the UV, preferably in the wavelength range of 320–1500 nm, in particular 350 to 800 nm. Where the terms "chromophore" or "dyestuff" are used in the context of this invention, they are not limited to the wavelength range of visible light, but are based on the groups A.

Groups A, which give $\Delta\Delta E$ values above 0.2, can be chosen from the radicals of the following classes of dyestuffs (cf. for example, G. Ebner and D. Schulz, Textilfärberei und Farbstoffe [Textile Dyeing and Dyestuffs], Springer-Verlag, Berlin Heidelberg 1989):

I. Azo dyestuffs
1. Monoazo dyestuffs, such as, for example
   C.I. Mordant Yellow 1
   C.I. Mordant Blue 78
   C.I. Disperse Blue 79
   C.I. Disperse Yellow 5
2. Disazo dyestuffs, such as, for example,
   C.I. Mordant Yellow 16
   C.I. Disperse Yellow 23
   C.I. Basic Brown 1
   C.I. Disperse Yellow 7

II. Quinonoid dyestuff
1. Quinonoid disperse and mordant dyestuffs such as, for example,
   C.I. Disperse Orange 11
   C.I. Disperse Blue 5
   C.I. Disperse Blue 7
   C.I. Mordant Violet 26
   C.I. Mordant Blue 23

III. Metal complex dyestuffs
   C.I. Ingrain Blue 14

IV. Meroquinonoide dyestuffs
1. Diphenylmethane dyestuffs, such as, for example,
   Basic Yellow 3
2. Triphenylmethane dyestuffs, such as, for example,
   C.I. Basic Violet 3
   C.I. Basic Green 4
   C.I. Mordant Blue 1
   C.I. Mordant Blue 28
3. Quinoneimine dyestuffs, such as, for example,
   C.I. Solvent Blue 22
4. Acridine dyestuffs, such as, for example,
   Acridine Orange 2 G
5. Thioxanthene dyestuffs; such as, for example,
   Pyronin G, C.I. 45005
6. Phenazine dyestuffs, such as, for example,
   C.I. Solvent Blue 7
7. Phenoxazine dyestuffs, such as, for example,
   C.I. Mordant Blue 10
8. Phenothiazine dyestuffs, such as, for example,
   C.I. Mordant Blue 51
9. Squaric acid dyestuffs, such as, for example, those known from EP-A 0 145 401

V. Polymethine dyestuffs comprising cationo, aniono and mero (=neutro)cyanines and hemicyanines, such as, for example,
   C.I. Disperse Yellow 31
   C.I. Disperse Blue 354
   C.I. Disperse Red 196
   C.I. Disperse Yellow 99

VI. Nitro and nitroso dyestuffs, such as, for example,
   C.I. Disperse Yellow 42
   C.I. Disperse Yellow 1

VII. Heterocyclic dyestuffs
1. Perinones, such as, for example,
   C.I. Disperse Yellow 58
2. Naphthalimides, such as, for example,
   Disperse Yellow 11
3. Quinophthalone, such as, for example,
   Disperse Yellow 54, Disperse Yellow 64
4. Coumarins, such as, for example, those known from DE 15 94 845, 16 70 999, 20 65 076
5. Pyrazolines, such as, for example, those known from DE 11 55 418, 14 45 705, 14 19 329
6. Stilbene dyestuffs, such as, for example,
   C.I. Fluorescent Brightener 30
   C.I. Fluorescent Brightener 46

In particular, the groups A can be chosen from the monovalent radicals of the following compounds:

  (I)

wherein

Het$^1$ denotes

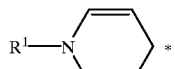  (1)

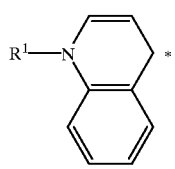  (2)

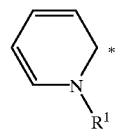  (3)

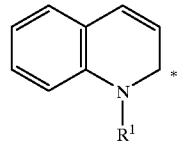  (4)

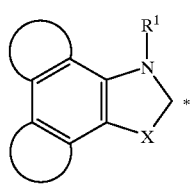  (5)

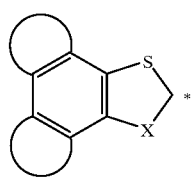  (6)

  (7)

(8) 

(9) 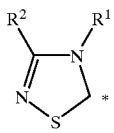

(10) 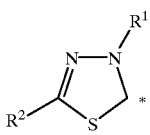

Z denotes CH—CH or N—N, n denotes zero or 1,

Het² denotes

(11) 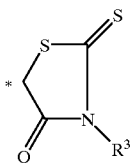

(12) 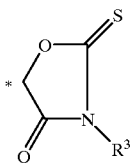

(13) 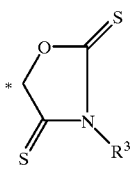

(14) 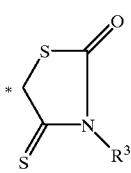

(15) 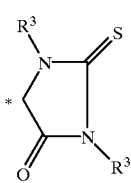

(16) 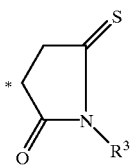

(17) 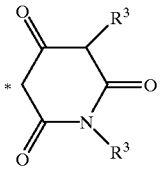

(18) 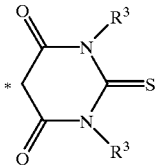

(19) 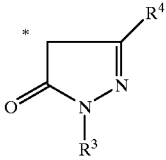

$R^1$ denotes $C_1$-$C_6$-alkyl, $C_2$-$C_6$-alkenyl, $C_5$-$C_{10}$-cycloalkyl or $C_7$-$C_{15}$-aralkyl, $R^2$ denotes $C_1$-$C_6$-alkyl, $C_1$-$C_4$-alkoxy, $C_6$-$C_{12}$-aryl, $C_6$-$C_{12}$-aryloxy, $C_1$-$C_6$-alkylthio, $C_6$-$C_{12}$-arylthio, mono- or di-$C_1$-$C_4$-alkylamino, $C_6$-$C_{12}$-arylamino, $C_1$-$C_4$-alkyl-$C_6$-$C_{12}$-arylamino or chlorine, $R^3$ denotes $C_1$-$C_6$-alkyl, $C_2$-$C_6$-alkenyl, $C_5$-$C_{10}$-cycloalkyl, $C_6$-$C_{12}$-aryl, $C_7$-$C_{15}$-aralkyl, $R^4$ denotes $C_1$-$C_6$-alkyl, $C_6$-$C_{12}$-aryl, CN, $COOR^3$, CO—$R^3$, X denotes O, S, Se, $NR^1$, $CR^8{}_2$, $R^8$ denotes $C_1$-$C_6$-alkyl, the asterisks characterize the position of the exocyclic C=C double bond and the curved lines in the structures (5) and (6) denote hydrogen or —CH=CH—CH=CH—;

$$Het^1(=Z)_n=Het^3 \quad (II)$$

wherein

(20) 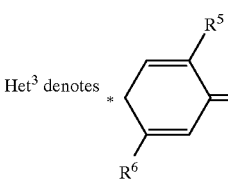

$R^5$ denotes hydrogen, $C_1$-$C_6$-alkyl, $C_1$-$C_6$-alkoxy, fluorine or chlorine, $R^6$ denotes hydrogen, $C_1$-$C_6$-alkyl, $C_1$-$C_6$-alkoxy, fluorine, chlorine, CN, $NO_2$, $NHCOR^3$ or $NHSO_2R^3$, Y denotes oxygen, $C(CN)_2$, $C(CN)COOR^3$ or

,

Het$^1$, Z, n, the asterisk and $R^3$ have the meaning given above under (I) and $R^{3'}$ independently of $R^3$ represents the meaning given above under $R^3$;

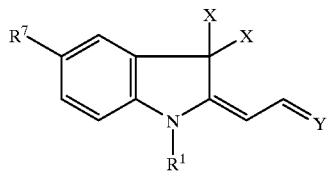 (III)

wherein

Y has the meaning given above under (II)—with the exception of oxygen—and additionally denotes

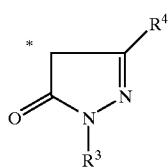 (21)

X, $R^1$, $R^3$, $R^4$ and the asterisk have the meaning given above under (I) and $R^7$ denotes hydrogen, $C_1$-$C_6$-alkyl, $C_1$-$C_6$-alkoxy, $COOR^3$, chlorine, $NO_2$ or CN;

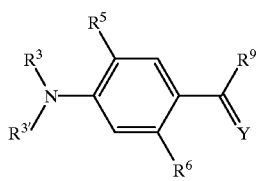 (IV)

wherein $R^3$ and $R^{3'}$ independently of one another have the meaning given above for $R^3$ under (I), $R^5$ and $R^6$ have the meaning given above under (II) and Y has the meaning given above under (III), $R^9$ denotes hydrogen, $C_1$-$C_6$-alkyl, $C_6$-$C_{12}$-aryl, CN or $COOR^3$ and furthermore additionally $R^{3'}$ denotes hydrogen,

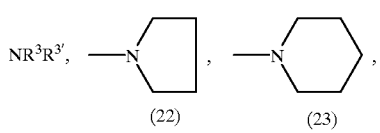

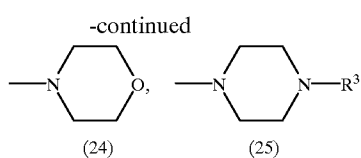

and $R^{3'}$ and $R^5$ together denote —(CH$_2$)$_2$—, —(CH$_2$)$_3$—, —C(CH$_3$)$_2$—CH$_2$—CH(CH$_3$)— or —OCH$_2$CH$_2$—;

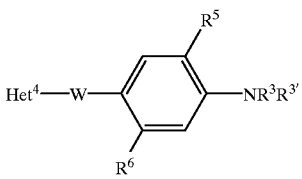 (V)

wherein

Het$^4$ denotes

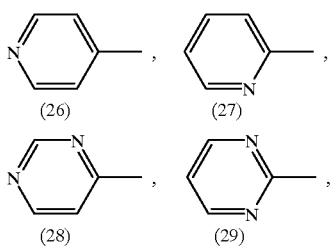

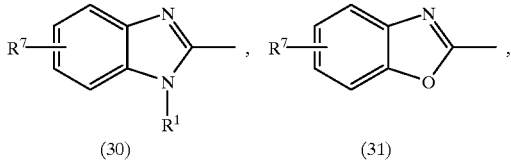

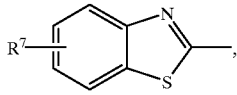 (32)

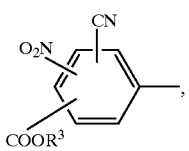 (33)

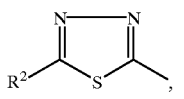 (34)

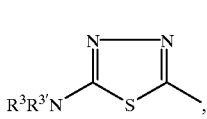 (35)

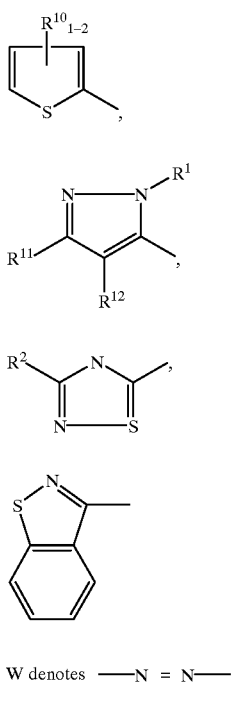

(36), (37), (38), (39)

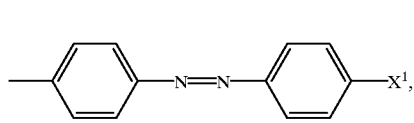

W denotes —N = N— or $R^{10}$ denotes CN, $NO_2$ or $COOR^3$, $R^{11}$ denotes $C_1$-$C_6$-alkyl, $C_1$-$C_6$-alkoxy, chlorine, amino, $C_1$-$C_7$-acylamino or di-$C_1$-$C_4$-alkylamino, $R^{12}$ denotes $C_1$-$C_6$-alkyl, $C_5$-$C_{12}$-aryl, CN or $COOR^3$, $R^{13}$ denotes hydrogen, CN or $NO_2$ and $R^1$, $R^2$, $R^7$, $R^3$, $R^{3'}$, $R^5$ and $R^6$ have the meaning given in the case of (I), (III) and (IV);

(VI)

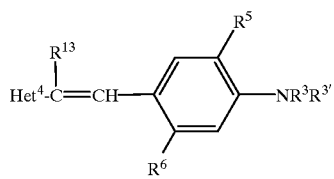

wherein $X^1$ denotes hydrogen, hydroxyl, mercapto, $CF_3$, $CCl_3$, $CBr_3$, halogen, cyano, nitro, $COOR^{19}$, $C_1$-$C_6$-alkyl, $C_5$-$C_{12}$-cycloalkyl, $C_1$-$C_{12}$-alkoxy, $C_1$-$C_{12}$-alkylthio, $C_6$-$C_{12}$-aryl, $C_6$-$C_{12}$-aryloxy, $C_6$-$C_{12}$-arylthio, $C_1$-$C_6$-alkylsulphonyl, $C_6$-$C_{12}$-arylsulphonyl, aminosulphonyl, $C_1$-$C_6$-alkylaminosulphonyl, phenylaminosulphonyl, aminocarbonyl, $C_1$-$C_6$-alkylaminocarbonyl, phenylaminocarbonyl, $NR^{19}$, $R^{20}$, NH—CO—$R^{19}$, NH—$SO_2$-$R^{19}$, NH—CO—$NR^{19}R^{20}$, NH—CO—O—$R^{19}$ or $SO_2$—$CF_3$, wherein $R^{19}$ and $R^{20}$ independently of one another represent hydrogen, $C_1$-$C_4$-alkyl or phenyl, wherein one of the radicals $R^1$ to $R^{13}$ (including $R^{3'}$), in particular one of the radicals $R^1$ and $R^3$, represents a single bond which allows linkage to the group $Q^1$, $Q^1$ then representing a single bond in the case of the radicals $R^1$, $R^3$ and $R^{3'}$.

Particularly preferred compounds (V) correspond to the formulae (Va)

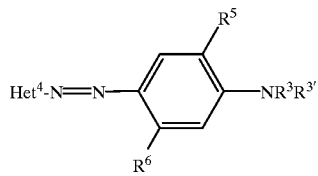

wherein $Het^4$ represents one of the structures 26 to 33, and (Vb)

Het$^4$-N=N- ... -$NR^3R^{3'}$ wherein $Het^4$ represents one of the structures 26, 27, 30, 32 or 34 to 39.

As described above, the group A is bonded to the main chains of the polymers according to the invention via the intermediate members $Q^1$, $T^1$ and $S^1$. The dyestuffs mentioned above can already contain these intermediate members in their entirety or in part; cf the legend to the substituents. Dyestuff radicals which are suitable as A are therefore to be understood as the dyestuffs shortened in each case by such intermediate members already contained in the product. On the other hand, if the dyestuffs do not contain the intermediate members $Q^1$, $T^1$ and $S^1$ or contain them only in part, they can be converted by appropriate reaction into the desired reactive derivatives, which are then suitable for building up the polymers according to the invention.

The unit —$Q^1$—$T^1$—$S^1$— can thus represent, for example, —$NR^0$—$(CH_2)_n$—O—. For a given group A, suitable compounds of the structure A—$NR^0$—$(CH_2)_n$—OH can be provided for introduction of A into the polymers according to the invention or into the monomers to be polymerized. (Analogous statements apply for another meaning of $Q^1$, $T^1$ and $S^1$). Such suitable compounds can thus include, for example, the following compounds:

(VII)

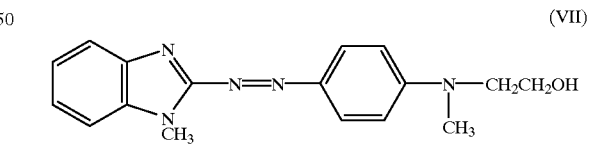

(VIII)

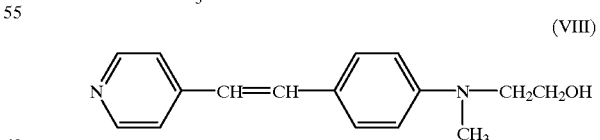

(IX)

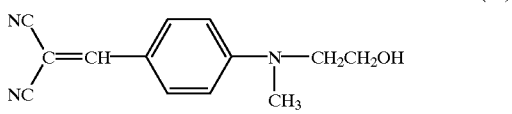

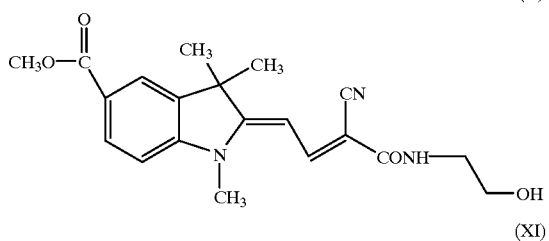

(X)

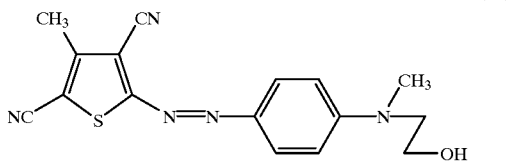

(XI)

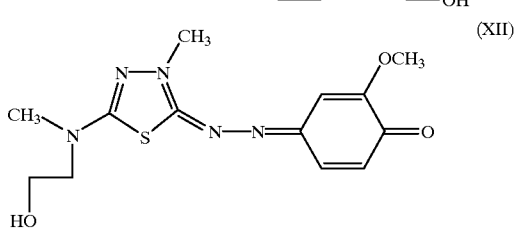

(XII)

Additionally to the above definitions, one of the substituents $R^1$ to $R^{13}$ (including $R^3$), in particular one of the radicals $R^1$ and $R^3$, per radical A denotes a single bond which allows linkage to the group $Q^1$.

The compounds
(1) $A\text{—}Q^1\text{—}T^1\text{—}S^1\text{—}H$
(2) $A\text{—}Q^1\text{—}T^1\text{—}S^1\text{—}OC\text{—}CH\text{=}CH_2$
(3) $A\text{—}Q^1\text{—}T^1\text{—}S^1\text{—}OC\text{—}C(CH_3)\text{=}CH_2$
(4) $A\text{—}Q^1\text{—}T^1\text{—}S^1\text{—}(CH_2)_n\text{—}OH$
(5) $A\text{—}Q^1\text{—}T^1\text{—}S^1\text{—}CH_2\text{—}CHOH\text{—}CH_3$
(6) $A\text{—}Q^1\text{—}T^1\text{—}S^1\text{—}CH_2\text{—}C(CH_3)_2\text{—}CH_2\text{—}OH$ wherein $A$, $Q^1$, $T^1$ and $S^1$ have the abovementioned meanings and n represents an integer from 2 to 12, and the acrylates and methacrylates of the compounds 4 to 6 are, to our knowledge, new and this invention therefore also relates to them. The compounds can be prepared by processes analogous to those for similar compounds.

The polymers according to the invention contain no groups A of the formula

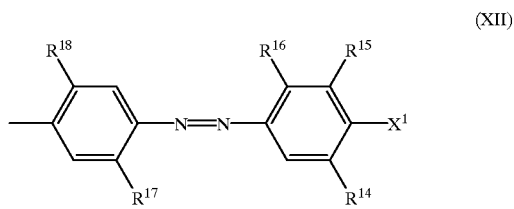

(XII)

wherein $R^{14}$ to $R^{16}$ independently of one another denote $C_1$-$C_6$-alkyl, hydroxyl, $C_1$-$C_6$-alkoxy, phenoxy, $C_1$-$C_6$-alkythio, phenylthio, halogen, $CF_3$, $CCl_3$, $CBr_3$, nitro, cyano, $C_1$-$C_6$-alkylsulphonyl, phenylsulphonyl, $COOR^1$, aminosulphonyl, $C_1$-$C_6$-alkylaminosulphonyl, phenylaminosulphonyl, aminocarbonyl, $C_1$-$C_6$-alkylaminocarbonyl or phenylaminocarbonyl, $R^{17}$ denotes halogen, $C_1$-$C_6$-alkyl, hydroxyl, $C_1$-$C_6$-alkoxy, phenoxy, $C_1$-$C_4$-acylamino or $C_1$-$C_4$-alkylsulphonylamino, $R^{18}$ denotes halogen, $C_1$-$C_6$-alkyl, hydroxyl, $C_1$-$C_6$-alkoxy or phenoxy and $X^1$ denotes hydrogen, hydroxyl, mercapto, $CF_3$, $CCl_3$, $CBr_3$, halogen, cyano, nitro, $COOR^{19}$, $C_1$-$C_6$-alkyl, $C_5$-$C_{12}$-cycloalkyl, $C_1$-$C_{12}$-alkoxy, $C_1$-$C_{12}$-alkylthio, $C_6$-$C_{12}$-aryl, $C_6$-$C_{12}$-aryloxy, $C_6$-$C_{12}$-arylthio, $C_1$-$C_6$-alkylsulphonyl, $C_6$-$C_{12}$-arylsulphonyl, aminosulphonyl, $C_1$-$C_6$-alkylaminosulphonyl, phenylaminosulphonyl, aminocarbonyl, $C_1$-$C_6$-alkylaminocarbonyl, phenylaminocarbonyl, $NR^{19}R^{20}$, $NH\text{—}CO\text{—}R^{19}$, $NH\text{—}SO_2\text{—}R^{19}$, $NH\text{—}CO\text{—}NR^{19}R^{20}$, $NH\text{—}CO\text{—}O\text{—}R^{19}$ or $SO_2\text{—}CF3$, wherein $R^{19}$ and $R^{20}$ independently of one another represent hydrogen, $C_1$-$C_4$-alkyl or phenyl.

Preferred mesogenic units M correspond to the formula

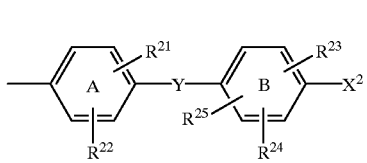

(XIV)

wherein $R^{21}$ to $R^{25}$ independently of one another denote hydrogen, halogen, $C_1$-$C_4$-alkyl, $C_1$-$C_4$-alkoxy, $CF_3$, nitro, $SO_2CH_3$, $SO_2NH_2$ or cyano, wherein at least one of the substituents $R^{21}$ to $R^{25}$ must be other than hydrogen, Y denotes a direct bond, —COO—, —OCO—, —CONH—, —NHCO—, —O—, —NH—, —N($CH_3$)— or —N=N— and $X^2$ denotes hydrogen, hydroxyl, mercapto, $CF_3$, $CCl_3$, $CBr_3$, halogen, cyano, nitro, $COOR^{19}$, $C_1$-$C_6$-alkyl, $C_5$-$C_{12}$-cycloalkyl, $C_1$-$C_{12}$-alkoxy, $C_1$-$C_{12}$-alkylthio, $C_6$-$C_{12}$-aryl, $C_6$-$C_{12}$-aryloxy, $C_6$-$C_{12}$-arylthio, $C_1$-$C_6$-alkylsulphonyl, $C_6$-$C_{12}$-arylsulphonyl, aminosulphonyl, $C_1$-$C_6$-alkylaminosulphonyl, phenylaminosulphonyl, aminocarbonyl, $C_1$-$C_6$-alkylaminocarbonyl, phenylaminocarbonyl, $NR^{19}R^{20}$, $NH\text{—}CO\text{—}R^{19}$, $NH\text{—}SO_2\text{—}R^{19}$, $NH\text{—}CO\text{—}NR^{19}R^{20}$, $NH\text{—}CO\text{—}O\text{—}R^{12}$ or $SO_2\text{—}CF_3$, wherein $R^{19}$ and $R^{20}$ independently of one another represent hydrogen, $C_1$-$C_4$-alkyl or phenyl, but wherein $R^{21}$ to $R^{25}$ all represent hydrogen when A corresponds to a radical of the formula (VI).

The preferred polymers according to the invention contain solely repeating units with the side groups I and II, and in particular preferably those of the formulae

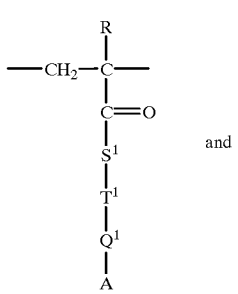

(XV)

and

-continued

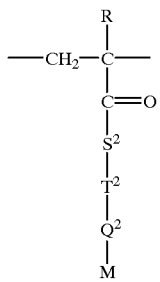
(XVI)

where R=H or methyl.

Preferred examples of the groups $T^1$ and $T^2$ are, independently of one another,

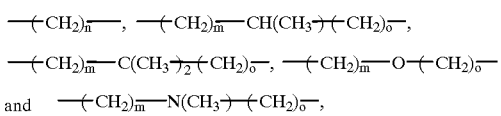

wherein
n is an integer from 2 to 6 and
m and o independently of one another are integers from 0 to 2, the total of which is at least 1.

$S^1T^1Q^1$ or $S^2T^2Q^2$ is also preferably

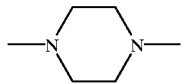

Possible preferred side groups II are, in particular, those of the formula

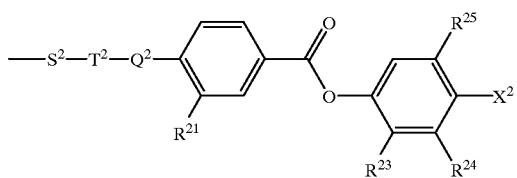
(XVII)

wherein
$X^2$, $T^2$, $Q^2$ and $R^{21}$ to $R^{25}$ have the abovementioned meanings.

Preferred monomers for introduction of the side groups II correspond to the formula

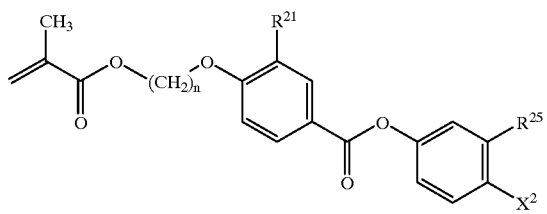
(XVIII)

wherein
n is an integer from 2 to 6,
$R^{21}$ and $R^{25}$ independently of one another represent H, F, Cl, Br, OH, $OCH_3$, $CH_3$, $CF_3$, $NO_2$ or CN and at least one of the substituents $R^{21}$ and $R^{25}$ must be other than H, and $X^2$ denotes H, F, Cl, Br, CN, $NO_2$, $COOR^{19}$, $C_5$-$C_{12}$-cycloalkyl, $C_1$-$C_{12}$-alkoxy or $C_6$-$C_{12}$-aryl and $R^{19}$, $R^{21}$ and $R^{25}$ have the abovementioned meaning.

Examples of such monomers are

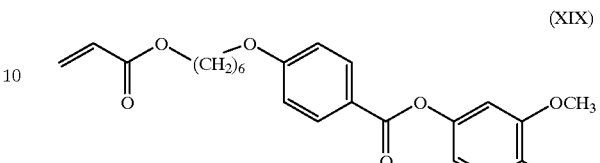
(XIX)

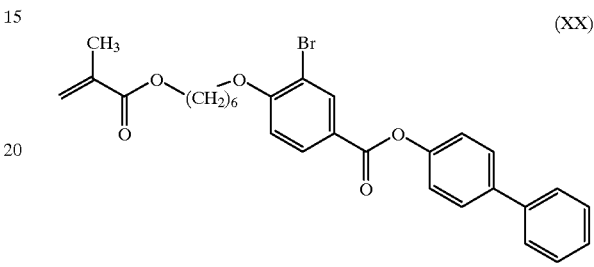
(XX)

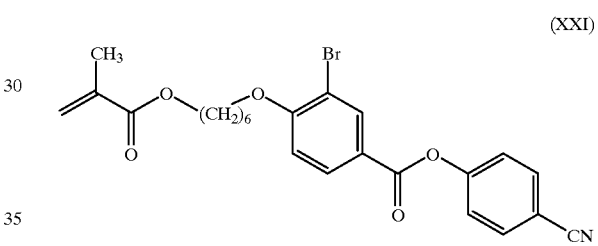
(XXI)

The main chain of the side group polymers is preferably formed by monomers which carry the side groups (I), by monomers which carry the side group (II) and, if appropriate, by further monomers, the proportion of monomers which contain the side group (I) being, in particular, 25 to 80 mol %, preferably 30 to 70 mol %, the proportion of monomers which contain the side group (II) being 20 to 75 mol %, preferably 30 to 70 mol %, and the proportion of the further monomers being 0 to 50 mol %, in each case based on the total of all the monomer units incorporated.

Possible "further" repeating units are all structural units which can be incorporated chemically into the side group polymer. They essentially serve merely to reduce the concentration of side groups I and II in the polymer and thus cause virtually a "dilution" effect. In the case of poly(meth) acrylates, the "further" monomers comprise ethylenically unsaturated copolymerizable monomers, which preferably carry α-substituted vinyl groups or β-substituted allyl groups, preferably styrene; and also, for example, styrenes which are chlorinated and alkylated or alkenylated on the nucleus, it being possible for the alkyl groups to contain 1 to 4 carbon atoms, such as, for example, vinyl-toluene, divinylbenzene, α-methylstyrene, tert-butylstyrenes and chlorostyrenes; vinyl esters of carboxylic acids having 2 to 6 carbon atoms, preferably vinyl acetate; vinylpyridine, vinylnaphthalene, vinylcyclohexane, acrylic acid and methacrylic acid and/or their esters (preferably vinyl, allyl and methallyl esters) having 1 to 4 carbon atoms in the alcohol component, their amides and nitriles, maleic anhydride, maleic acid half-esters and diesters having 1 to 4 carbon atoms in the alcohol component and half-amides and diamides, and cyclic imides, such as N-methylmaleimide or N-cyclohexylmaleimide; and allyl compounds, such as allylbenzene and allyl esters, such as allyl acetate, diallyl phthalate, diallyl isophthalate, diallyl fumarate, allyl carbonates, diallyl carbonates, triallyl phosphate and triallyl cyanurate.

Preferred "further" monomers correspond to the formula

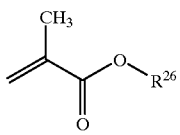

(XXII)

wherein $R^{26}$ represents an optionally branched $C_1$-$C_6$-alkyl radical or a radical containing at least one further acrylic radical.

The polymers according to the invention can also contain more than one side group which falls under the definition of (I), or more than one side group which falls under the definition of (II), or several side groups of the definition both of (I) and of (II), and of these one side group of the definition (I) can also correspond to the formula XIII. If side chains of the structure (I) and (II) are present, at least one group $Q^1$ or $Q^2$ advantageously has the meaning —O—$C_6H_4$—COO— or —O—$C_6H_4$—CONR$^{19}$.

The polymers according to the invention preferably have glass transition temperatures Tg of at least 40° C. The glass transition temperature can be determined, for example, by the method of B. Volhmer, Grundriβ der Makromolekularen Chemie [Principles of Macromolecular Chemistry], pages 406–410, Springer-Verlag, Heidelberg 1962.

The polymers according to the invention in general have a molecular weight, determined as the weight average, of 5,000 to 2,000,000, preferably 8,000 to 1,500,000, determined by gel permeation chromatography (calibrated with polystyrene).

The structural elements of high shape anisotropy and high anisotropy of the molecular polarizability are the prerequisite for high values of optical anisotropy. The intermolecular interactions of the structural elements (I) and (II) are established by the structure of the polymers such that the formation of liquid crystal states of order is suppressed and optically isotropic, transparent non-scattering films can be produced. On the other hand, the intermolecular interactions are nevertheless strong enough to cause a photochemically induced, cooperative, directed reorientation process of the photochromic and non-photochromic side groups on irradiation with polarized light.

Interaction forces which are sufficient for the photoinduced change in configuration of the side group (I) to cause a reorientation of the side group (II) in the same direction—so-called cooperative reorientation—preferably occur between the side groups (I) and (II).

In the optically isotropic amorphous photochromic polymers, extremely high values of the optical anisotropy can be induced ($\Delta n$=0.01 to 0.2, preferably 0.01 to 0.1). The values are comparable to those which have been obtained in monodomains of liquid crystal polymers, or are even greater than these. They are significantly greater in comparison with amorphous polymers without these structural elements.

States of order are generated and modified in the side group polymers, and their optical properties are thus modulated, by the influence of actinic light.

Linearly polarized light, the wavelength of which is in the range of the absorption band of the side groups (I) whose configuration can be varied by photoinduction is preferably used as the light.

The preparation of the side group monomers and their polymerization can be carried out by processes known from the literature (for example DD 276 297, DE 3 808 430, Makromolekulare Chemie [Macromolecular Chemistry] 187, 1327–1334 (1984), SU 887 574, Europ. Polym. 18 561 (1982) and Liq. Cryst. 2, 195 (1987)).

Isotropic films can be produced without the need for expensive orientation processes utilizing external fields and/or surface effects. They can be applied to substrates by spin coating, dipping, casting or other coating processes which are easy to control technologically, can be introduced between two transparent sheets by pressing or flowing in, or can simply be prepared as a self-supporting film by casting or extrusion. Such films can also be produced from liquid crystal polymers which contain the structural elements in the context described by sudden cooling, that is to say by a cooling rate of >100 K/minute, or by rapid stripping of the solvent.

The layer thickness is preferably between 0.1 μm and 1 mm, in particular between 0.5 and 100 μm.

The photoinduced orientation of the side groups or the writing of information is effected by irradiation with actinic light suitable for the group A whose configuration can be varied by photoinduction. This leads to an angle-dependent photoselection, which causes reorientation of the photochromic groups and—by a cooperative effect—a continuous reorientation of the permanently shape-anisotropic side groups M in the same direction up to the maximum of perpendicular with respect to the electrical vector of the stimulating light.

The exposure to light can take place over the whole surface or locally with linearly polarized, coherent or non-coherent, monochromatic light, the wavelength of which is in the absorption range of the side groups A whose configuration can be varied by photoinduction.

The information can be written in point form with a laser or in unstructured form over the whole surface with a laser or a lamp or using a mask or by writing in a holographic refractive index grid at an intensity of 1 to 500 mW/cm² over a period of between 1 and 30,000 seconds.

The reorientation process is exceptionally effective. The change in birefringence Δn which can be achieved below Tg is preferably 0.01 to 0.20, in particular 0.05 to 0.10.

The high values of the photochemically induced birefringence and of the photochemically induced dichroism result from the molecular structure of the side groups and the cooperative mechanism of the photoinduced orientation to a state of the same macroscopic orientation of the photochromic and non-photochromic but permanently shape-anisotropic side groups.

The preferred orientation can be chosen as desired, and depends solely on the choice of the direction of the electrical vector of the stimulating light with reference to the polymer substance. The extent of the orientation at a constant temperature and wavelength depends solely on the irradiated energy, which can be varied either via the time or, within certain limits, via the output of the light source. The orientation, the birefringence and the dichroism are thus parameters which can be chosen as desired and can be reproduced exactly under constant framework conditions during repeated writing and deletion.

A reproducible, defined, continuously variable birefringence of long-term stability can be produced in the side chain polymers. It can be shown as a defined contrast in transmission in the polarized light. If polymers with side groups with dichroic properties are used, a dichroism of the absorption or of the emission can correspondingly be produced reproducibly and in a defined and continuously variable manner. A uniform orientation is produced in the entire polymer film by uniform irradiation conditions. If the irradiation conditions, such as energy dose and polarization direction, vary locally, a film which is structured in respect of the preferred orientation of the side groups is produced, which leads to pixels of different optical anisotropy.

The preferred direction in the orientation distribution of the optically anisotropic film can be reversed again by exposure to non-polarized actinic light, and the optical isotropy along the perpendicular to the surface can be reestablished. Renewed irradiation with the same source but a changed position of the electrical vector with reference to the polymer film leads to a modification of the direction and magnitude of optical anisotropy. The system can in this way be switched repeatedly between two different states with respect to the direction and magnitude of the optical anisotropy.

On the basis of these effects, a medium for reversible, optical data storage is in principle available with the polymers described. As with the production of the films, all measures for reestablishing the monodomain are dispensed with even after deletion of the information.

The polymers can be used for digital or analog data storage in the broadest sense, for example for optical signal processing, for Fourier transformation and folding or in coherent optical correlation techniques. The lateral resolution is limited by the wavelength of the reading light. It allows a pixel size of 1 to 100 μm.

This property makes the polymers particularly suitable for processing images and for information processing by means of holograms, reproduction of which can be effected by illuminating with a reference beam. The interference pattern of two monochromatic coherent light sources with a constant phase relationship can be stored analogously and a higher storage density can be produced in the storage medium owing to the relationship between the electrical vector of the light and the associated preferred direction. Three-dimensional holographic images can correspondingly be stored. Read-out is achieved by illuminating the hologram with monochromatic, coherent light. In the case of analog storage, grey scale values can be established continuously and with local resolution. Read-out of information stored in analog form is effected in polarized light, it being possible to bring out the positive or negative image, depending on the position of the polarizers. In this case, on the one hand the contrast of the film produced by the phase shift of the ordinary and extraordinary beam can be utilized between two polarizers, the planes of the polarizer advantageously forming an angle of 45° to the plane of polarization of the writingin light and the plane of polarization of the analyser being either perpendicular or parallel to that of the polarizer. Another possibility is detection of the deflection angle of the reading light caused by induced birefringence.

The polymers can be used as optical components which can be passively or optically switchable. Thus, the high photoinduced optical anisotropy can be utilized for modulation of the intensity and/or of the state of polarization of light. Components which have imaging properties comparable to lenses or gratings can correspondingly be produced from a polymer film by holographic structuring. The polymers can furthermore be employed for the production of polarizers.

The invention thus also relates to the use of the polymers described for optical components. Polarizers are also to be regarded as such optical components.

The polymers according to the invention can be prepared in the customary manner by free radical copolymerization of the monomers in suitable solvents, such as, for example, aromatic hydrocarbons, such as toluene or xylene, aromatic halogenated hydrocarbons, such as chlorobenzene, ethers, such as tetrahydrofuran and dioxane, ketones, such as acetone and cyclohexanone, and/or dimethylformamide, in the presence of polymerization initiators which supply free radicals, such as, for example, azodiisobutyronitrile or benzoyl peroxide, at elevated temperatures, as a rule at 30 to 130° C., preferably 40 to 70° C., as far as possible with exclusion of water and air. They can be isolated by precipitation with suitable agents, for example methanol. The products can be purified by reprecipitation, for example with chloroform/methanol.

The polymers according to the invention can form self-supporting films.

Preferably, however, they are applied to carrier materials, for example glass or films of plastic. This can be effected by various techniques known per se, the process being chosen according to whether a thick or thin layer is desired. Thin layers can be produced, for example, by spin coating or knife coating from solutions or the melt, and thicker layers can be produced by filling prefabricated cells, melt pressing or extrusion.

The percentage data in the following examples in each case relate to the weight—unless stated otherwise.

EXAMPLES

Example 1

A $10^{-3}$ molar solution of 4-(N-methyl-N'-hydroxyethyl)-amino-4'-nitro-azobenzene (molecular weight 300) (solution A) and a 1 molar solution of 1,3-dinitrobenzene (molecular weight 168) (solution B) are prepared in dioxane. The 1,3-dinitrobenzene must be very pure, and if necessary purified by crystallization from dioxane. To prepare solution C, 30 mg of the dyestuff are weighed into a 100 ml pipetting flask and topped up with solution B. Solution C shows a clearly perceptible deepening in colour compared with solutions A and B. The longwave absorption edges of the three solutions are recorded with a UV VIS spectrophotometer (Perkin-Elmer, Lambda 3 model) in a 1 cm cell starting from long wavelengths up to the pen buffer. 3 absorption edges which are separated well from one another and run essentially parallel are obtained. The full deflection of the pen defines the extinction 1.0. The edge of solution C reaches the extinction value $E_{solution\ C}=0.8$ at $\lambda=575$ nm, from which the second readout wavelength of $\lambda+50=625$ nm results. The associated extinction values are $\lambda=575$ nm for $E_{solution\ A}=0.185$ and for $E_{solution\ B}=0.06$. At 625 nm, the extinctions are $E_{solution\ C}=0.070$, $E_{solution\ A}=0.05$ and $E_{solution\ B}=0.025$. The extinction differences $\Delta E_C=0.73$, $\Delta E_A=0.05$ and $\Delta E_B=0.025$ result from these. From this, it follows that $\Delta\Delta E=0.56$. The following results are found for the following compounds by the same method:

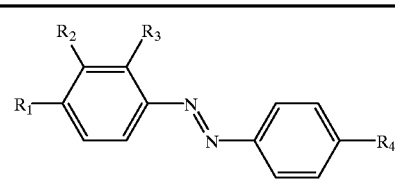

| Ex. | R¹ | R² | R³ | R⁴ | ΔΔE |
|---|---|---|---|---|---|
| 2 | CH₃ | H | H | N(CH₃)C₂H₄OH | 0.18 |
| 3 | OCH₃ | H | H | N(CH₃)C₂H₄OH | 0.22 |
| 4 | Cl | H | H | N(CH₃)C₂H₄OH | 0.24 |
| 5 | SO₂NH₂ | H | H | N(CH₃)C₂H₄OH | 0.34 |
| 6 | CN | H | H | N(CH₃)C₂H₄OH | 0.40 |
| 7 | CN | H | CN | N(CH₃)C₂H₄OH | 0.43 |
| 8 | CN | CN | H | N(CH₃)C₂H₄OH | 0.54 |
| 9 | H | H | H | N(C₂H₅)C₂H₄OH | 0.17 |
| 10 | OCH₃ | H | H | N(C₂H₅)C₂H₄OH | 0.24 |
| 11 | Cl | H | H | N(C₂H₅)C₂H₄OH | 0.28 |
| 12 | CF₃ | H | H | N(C₂H₅)C₂H₄OH | 0.39 |
| 13 | NO₂ | H | H | N(C₂H₅)C₂H₄OH | 0.53 |
| 14 | NO₂ | H | H | OCH₃ | 0.09 |
| 15 | CH₃ | H | H | N(CH₃)₂ | 0.17 |
| 16 | OCH₃ | H | H | N(CH₃)₂ | 0.19 |

| Ex. | R¹ | R² | R³ | R⁴ | ΔΔE |
|---|---|---|---|---|---|
| 17 | H | H | H | N(CH₃)₂ | 0.21 |
| 18 | Cl | H | H | N(CH₃)₂ | 0.24 |
| 19 | Br | H | H | N(CH₃)₂ | 0.28 |
| 20 | CN | H | H | N(CH₃)₂ | 0.48 |
| 21 | NO₂ | H | H | N(CH₃)₂ | 0.56 |

Example 22

The dyestuff from Example 1 is reacted with methacryloyl chloride in methylene chloride in the presence of potash by the process known from the literature, the resulting ester is purified by column chromatography over silica gel and the ΔΔE value of 0.48 is determined by the process described in Example 1.

If the dyestuffs from Examples 4 or 6 are used instead of the dyestuff from Example 1 and the procedure is otherwise as described above, ΔΔE values of 0.27 and 0.47 respectively are obtained.

This thus shows that only group A is important, but it may be substituted within wide limits and as a result varies the ΔΔE values.

Example 23

If a 1 molar solution of 4cyano-4'-hydroxybiphenyl is used in the determination process in Example 1 instead of the 1,3-dinitrobenzene standard used there, the ΔΔA value is 0.37, and if N—(4-cyanophenyl)-4-carbamidophenyl-2-oxy-ethylene-methacrylic acid ester is employed instead of the 1,3-dinitrobenzene standard, the ΔΔE value is 0.47.

This shows that the standard can also be replaced, and in the individual case can be adapted to the peculiarities of the system.

Example 24

Copolymers of the methacrylic acid esters of the dyestuffs mentioned in Examples 1 to 10 with equimolar amounts of
a) N—(4-cyanophenyl)-4'-carbamidophenyl)-2-oxyethylene-methacrylic acid ester and
b) 4-cyano-biphenyl-4'-oxyethylene-methacrylic acid ester are polymerized in chloroform with AIBN as a free radical initiator. Measurement specimens of the copolymers are produced on glass plates 2×2 cm in size and of thickness 1.1 mm by placing them in a spin coater (model Süss RC 5) and coating them with 0.2 ml of a solution of 150 g of the polymers shown below in 1 liter of absolute tetrahydrofuran at 2000 rpm in the course of 10 seconds. The layer is 0.9 μ thick, transparent and amorphous. Between crossed polarizers, the surface appears uniformly dark. No signs of polarizing regions are observed.

The measurement plates are exposed to light from an Ar ion laser with an output of 60 mW at a wavelength of 514 nm, a birefringence building up, which is measured. The results obtained are:

| Dyestuff example | ΔΔE | Δn Copolymer 24a | Copolymer 24b |
|---|---|---|---|
| 10 | 0.17 | | 0.011 |
| 2 | 0.18 | 0.021 | |
| 3 | 0.22 | 0.089 | 0.079 |
| 4 | 0.24 | | 0.019 |
| 6 | 0.40 | 0.063 | 0.074 |
| 7 | 0.43 | 0.038 | 0.077 |
| 8 | 0.54 | 0.024 | |
| 1 | 0.56 | 0.074 | 0.116 |

The example shows that the ΔΔE value correctly predicts the representatives with a high change in birefringence independently of the choice of the group M.

What is claimed is:

1. A polymer having a main chain as a backbone and, branching therefrom, covalently bonded side groups of the formulae

wherein $S^1$ and $S^2$ denote the atoms O or S or the radical $NR^0$, or COO $R^0$ denotes hydrogen or $C_1$-$C_4$-alkyl, $T^1$ and $T^2$ denote the radical $(CH_2)_n$, which can optionally be interrupted by —O—, —$NR^0$— or —$OSiR^0{}_2O$— and/or can optionally be substituted by methyl or ethyl, $Q^1$ and $Q^2$ denote a direct single bond, —O—, —COO—, —OCO—, —$CONR^0$, —$NR^-CO^0$— or —$NR^0$—, or $S^1T^1Q^1$ or $S^2T^2Q^2$ denotes a bivalent group of the formula

A denotes a unit which can absorb electromagnetic radiation,

M denotes a mesogenic unit anisotropic in shape and n denotes an integer from 2 to 12, wherein A has an extinction modulus ΔΔE of greater than 0.2, measured on a compound of the formula A—$Q^1H$ or $AQ^1T^1S^1H$ by 6 individual measurements:

A) A—$Q^1H$ or $AQ^1T^1S^1H$ in the lowest possible concentration in a solvent of the lowest possible polarity, B) standard in the highest possible concentration in the same solvent, C) A—$Q^1H$ or $AQ^1T^1S^1H$ and standard in the concentration as above in the same solvent measured in each case twice at the longer-wavelength edge of the absorption curve, and measured once at a wavelength λ at which the extinction of curve C is 0.8, and once at a wavelength λ+50 nm, the three differences of the extinction $\Delta E=E_{\lambda+50}$ being obtained for the ingredients A) to C), and the three values $\Delta E_A$ and $\Delta E_B$ and $\Delta E_C$ being obtained, the value $\Delta\Delta E$ sought then being the difference $\Delta\Delta E=\Delta E_C-(\Delta E_B+\Delta E_A)$, and with the proviso that the polymer does not include group A having the formula:

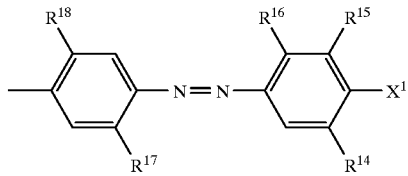

wherein $R^{14}$ to $R^{16}$ independently of one another denote $C_1$-$C_6$-alkyl, hydroxyl, $C_1$-$C_6$-alkoxy, phenoxy, $C_1$-$C_6$-alkylthio, phenylthio, halogen, $CF_3$, $CCl_3$, $CBr_3$, nitro, cyano, $C_1$-$C_6$-alkylsulphonyl, phenylsulphonyl, $COOR^1$, aminosulphonyl, $C_1$-$C_6$-alkylaminosulphonyl, phenylaminosulphonyl, aminocarbonyl, $C_1$-$C_6$-alkylaminocarbonyl or phenylaminocarbonyl, $R^{17}$ denotes halogen, $C_1$-$C_6$-alkyl, hydroxyl, $C_1$-$C_6$-alkoxyl, phenoxy, $C_1$-$C_4$-acylamino or $C_1$-$C_4$-alkylsulphonylamino, $R^{18}$ denotes halogen, $C_1$-$C_6$-alkyl, hydroxyl, $C_1$-$C_6$-alkoxy or phenoxy and $X^1$ denotes hydrogen, hydroxyl, mercapto, $CF_3$, $CCl_3$, $CBr_3$, halogen, cyano, nitro, $COOR^{19}$, $C_1$-$C_6$-alkyl, $C_5$-$C_{12}$-cycloalkyl, $C_1$-$C_{12}$-alkoxy, $C_1$-$C_{12}$-alkylthio, $C_6$-$C_{12}$-aryl, $C_6$-$C_{12}$-aryloxy, $C_6$-$C_{12}$-arylthio, $C_1$-$C_6$-alkylsulphonyl, $C_6$-$C_{12}$-arylsulphonyl, aminosulphonyl, $C_1$-$C_6$-alkylaminosulphonyl, phenylaminosulphonyl, aminocarbonyl, $C_1$-$C_6$-alkylaminocarbonyl, phenylaminocarbonyl, $NR^{19}R^{20}$, NH-CO-$R^{19}$, NH-$SO_2$-$R^{19}$, NH-CO-NR-$^{19}R^{20}$, NH-CO-O-$R^{19}$ or $SO_2$-$CF3$, wherein $R^{19}$ and $R^{20}$ independently of one another represent hydrogen, $C_1$-$C_4$-alkyl or phenyl.

2. A polymer having a main chain as a backbone and, branching therefrom, covalently bonded side groups of the formulae

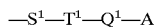 (I) and

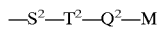 (II)

wherein $S^1$ and $S^2$ denote the atoms O or S or the radical $NR^0$, or COO $R^0$ denotes hydrogen or $C_1$-$C_4$-alkyl, $T^1$ and $T^2$ denote the radical $(CH_2)_n$, which can optionally be interrupted by —O—, —$NR^0$— or —$OSiR^0{}_2O$— and/or can optionally be substituted by methyl or ethyl, $Q^1$ and $Q^2$ denote a direct single bond, —O—, —COO—, —OCO—, —$CONR^0$, —$NR^-CO^0$— or —$NR^0$—, or $S^1T^1Q^1$ or $S^2T^2Q^2$ denotes a bivalent group of the formula

A denotes a unit which can absorb electromagnetic radiation,

M denotes a mesogenic unit anisotropic in shape and n denotes an integer from 2 to 12, wherein A has an extinction modulus $\Delta\Delta E$ of greater than 0.2, measured on a compound of the formula A—$Q^1$H or $AQ^1T^1S^1$H by 6 individual measurements:

A) A—$Q^1$H or $AQ^1T^1S^1$H in the lowest possible concentration in a solvent of the lowest possible polarity, B) standard in the highest possible concentration in the same solvent, C) A—$Q^1$H or $AQ^1T^1S^1$H and standard in the concentration as above in the same solvent measured in each case twice at the longer-wavelength edge of the absorption curve, and measured once at a wavelength λ at which the extinction of curve C is 0.8, and once at a wavelength λ+50 nm, the three differences of the extinction $\Delta E=E_{\lambda+50}$, being obtained for the ingredients A) to C), and the three values $\Delta E_A$ and $\Delta E_B$ and $\Delta E_C$ being obtained, the value $\Delta\Delta E$ sought then being the difference $\Delta\Delta E=\Delta E_C-(\Delta E_B+\Delta E_A)$, with the proviso that said group A does not include an unsubstituted

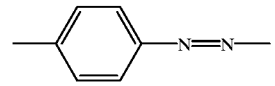

and with the further proviso that the ploymer does not include group A having the formula:

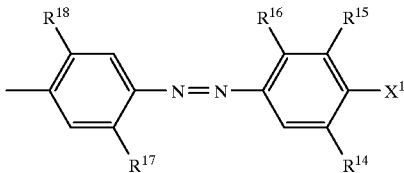

wherein $R^{14}$ to $R^{16}$ independently of one another denote $C_1$-$C_6$-alkyl, hydroxyl, $C_1$-$C_6$-alkoxy, phenoxy, $C_1$-$C_6$-alkylthio, phenylthio, halogen, $CF_3$, $CCl_3$, $CBr_3$, nitro, cyano, $C_1$-$C_6$-alkylsulphonyl, phenylsulphonyl, $COOR^1$, aminosulphonyl, $C_1$-$C_6$-alkylaminosulphonyl, phenylaminosulphonyl, aminocarbonyl, $C_1$-$C_6$-alkylaminocarbonyl or phenylaminocarbonyl, $R^{17}$ denotes halogen, $C_1$-$C_6$-alkyl, hydroxyl, $C_1$-$C_6$-alkoxy, phenoxy, $C_1$-$C_4$-acylamino or $C_1$-$C_4$-alkylsulphonylamino, $R^{18}$ denotes halogen, $C_1$-$C_6$-alkyl, hydroxyl, $C_1$-$C_6$-alkoxy or phenoxy and $X^1$ denotes hydrogen, hydroxyl, mercapto, $CF_3$, $CCl_3$, $CBr_3$, halogen, cyano, nitro, $COOR^{19}$, $C_1$-$C_6$-alkyl, $C_5$-$C_{12}$-cycloalkyl, $C_1$-$C_{12}$-alkoxy, $C_1$-$C_{12}$-alkylthio, $C_6$-$C_{12}$-aryl, $C_6$-$C_{12}$-aryloxy, $C_6$-$C_{12}$-arylthio, $C_1$-$C_6$-alkylsulphonyl, $C_6$-$C_{12}$-arylsulphonyl, aminosulphonyl, $C_1$-$C_6$- alkylaminosulphonyl, phenylaminosulphonyl, aminocarbonyl, $C_1$-$C_6$-alkylaminocarbonyl, phenylaminocarbonyl, $NR^{19}R^{20}$, $NH$-$CO$-$R^{19}$, $NH$-$SO_2$-$R^{19}$, $NH$-$CO$-$NR^{19}R^{20}$, $NH$-$CO$-$O$-$R^{19}$ or $SO_2$-$CF3$, wherein $R^{19}$ and $R^{20}$ independently of one another represent hydrogen, $C_1$-$C_4$alkyl or phenyl.

* * * * *